(12) United States Patent
Kwak et al.

(10) Patent No.: US 7,901,716 B2
(45) Date of Patent: Mar. 8, 2011

(54) ACTIVE FRACTION HAVING ANTI-CANCER AND ANTI-METASTASIS ISOLATED FROM LEAVES AND STEMS OF GINSENG

(75) Inventors: Tae Hwan Kwak, Yongin-si (KR);
Myoung Sook Shin, Seongnam-si (KR);
Ji Yeon Kim, Seongnam-si (KR);
Jong-Kook Park, Daejeon (KR)

(73) Assignee: MD Bioalpha Co., Ltd. (KR)

( * ) Notice: Subject to any disclaimer, the term of this patent is extended or adjusted under 35 U.S.C. 154(b) by 498 days.

(21) Appl. No.: 10/515,960

(22) PCT Filed: May 28, 2003

(86) PCT No.: PCT/KR03/01042
§ 371 (c)(1),
(2), (4) Date: Aug. 1, 2005

(87) PCT Pub. No.: WO03/099308
PCT Pub. Date: Dec. 4, 2003

(65) Prior Publication Data
US 2006/0034951 A1 Feb. 16, 2006

(30) Foreign Application Priority Data
May 28, 2002 (KR) .......................... 10-2002-0029469

(51) Int. Cl.
*A61K 36/00* (2006.01)
*A61K 36/254* (2006.01)
*A61K 9/00* (2006.01)
*A61K 47/00* (2006.01)

(52) U.S. Cl. .......... 424/728; 424/725; 424/400; 424/439

(58) Field of Classification Search .......... None
See application file for complete search history.

(56) References Cited

U.S. PATENT DOCUMENTS

| 4,005,191 | A | * | 1/1977 | Clark | 424/687 |
| 6,077,830 | A | * | 6/2000 | Vertesy et al. | 514/25 |
| 6,432,454 | B1 | * | 8/2002 | Shan et al. | 424/728 |
| 6,558,694 | B2 | * | 5/2003 | Brooks et al. | 424/449 |
| 7,034,024 | B1 | * | 4/2006 | Prevost et al. | 514/249 |

FOREIGN PATENT DOCUMENTS

| JP | 61109732 A | * | 5/1986 |
| KR | 19960040368 | | 12/1996 |
| KR | 100144130 B1 | | 4/1998 |
| KR | 1020000014189 A | | 3/2000 |
| KR | 1020010050186 A | | 6/2001 |

OTHER PUBLICATIONS

DW ACC 1985-239827, Aug. 1985, JP, Maeda M.*
DW-ACC 2001-603112, Dec. 1997, Derwent and CN, Ma et al.*
Goo, et al., "Chemical Properties and Anti-Complementary Activities of Polysaccharide Fractions from Roots and Leaves of Panax Ginseng," Planta Medica, vol. 55, pp. 9-12 (1989).
Yi, et al., "Inductive Differentiation Effect of Ginsenosides on Human Acute Non-lymphocytic Leukemia Cells in 58 Patients," British Library-The World's Knowledge, 13(12), pp. 722-724 (Abstract Only), Dec. 1993.
Duo et al. "Six New Dammarane-Type Triterpene Saponins from the Leaves of Panax ginseng," Chem. Pharm. Bull., vol. 49(4), pp. 442-446 (2001). (Abstract Only).
Liu CX and Xiao GP, "Recent Advances on Ginseng Research in China," J. Ethnopharmacol. 36(1), pp. 27-38 (1992). (Abstract Only).
Han, B.H. et al., Studies on the Antioxidant Components of Korean Ginseng (IV) Antifatigue Active Components, Yakhak Hoeji (Korean Pharmaceutical Bulletin), 1984, 28(4): 231-235. (English abstract only).
Bendelac, A. et al., Mouse CD1-specific NK1 T Cells: Development, Specificity, and Function, Annu. Rev. Immunol. 1997; 15: 535-562.
Blumenkrantz, N. et al., New Method for Quantitative Determination of Uronic Acids, Anal Biochem. 1973; 54(2): 484-489.
Dubois, M. et al., Colorimetric Method for Determination of Sugars and Related Substances, Anal. Chem., 1956, 28 (3): 350-356.
Fidler, I. J., Cancer Metastasis, British Medical Bulletin, 1991, 47: 157-177.
Herberman, R.B., Possible role of natural killer cells and other effector cells in immune surveillance against cancer, J. Invest Dermatol. 1984, 83(1 Suppl): 137s-140s.
Jones, T.M. et al., A Gas Chromatographic Method for the Determination of Aldose and Uronic Acid Constituents of Plant Cell Wall Polysaccharides, Plant Physiol. 1972, 49(6): 926-936.
Lowry, O.H. et al., Protein Measurement with the Folin Phenol Reagent, J. Biol. Chem. 1951; 193: 265-275.
Schantz, S. P. et al., Evidence for the role of natural immunity in the control of metastatic spread of head and neck cancer, Cancer Immunol Immunother. 1987; 25: 141-148.
Shin, K.S. et al., Rhamnogalacturonan II from the leaves of Panax ginseng C.A. Meyer as a macrophage Fc receptor expression-enhancing polysaccharide, Carbohydrate Res. 1997, 300(3): 239-249.
Sun, X.B. et al., Purification of an Anti-Ulcer Polysaccharide from the Leaves of Panax ginseng, Planta Med. 1992, 58: 445-8.
Yoo, Y.C. et al., MDP-Lys(L18), a lipophilic derivative of muramyl dipeptide, inhibits the metastasis of haematogenous and non-haematogenous tumours in mice, Vaccine, 1994, 12(2): 175-180.
Yoo, Y.C. et al., Bovine lactoferrin and lactoferricin, a peptide derived from bovine lactoferrin, inhibit tumor metastasis in mice, Jpn J. Cancer Res. 1997, 88: 184-90.

* cited by examiner

*Primary Examiner* — Christopher R Tate
*Assistant Examiner* — Randall O Winston
(74) *Attorney, Agent, or Firm* — Cantor Colburn LLP

(57) ABSTRACT

Provided is a composition that contains, as an active ingredient, an extract or polysaccharides separated from the leaves and/or stems of plants belonging to *Panax* genus, for an anticancer drug or its adjuvant, having an effect on the activity of hematopoiesis enhancement, cancer metastasis inhibition, bone marrow defense, etc. . . . , and a process for preparation of the extract from the leaves and/or stems of plants belonging to *Panax* genus.

24 Claims, 11 Drawing Sheets

ACTIVE FRACTION HAVING ANTI-CANCER AND ANTI-METASTASIS ISOLATED FROM LEAVES AND STEMS OF GINSENG

TECHNICAL FIELD

The present invention relates to a composition containing, as an effective ingredient, an extract from the leaves and/or stems of plants belonging to *Panax* genus and a process for preparation of the polysaccharides, and more particularly a composition containing polysaccharides separated from the leaves and/or stems of the *Panax* genus plants, which can work as an anticancer drug and/or a cancer metastasis inhibitor by activating immune cells, such as natural killer (NK) T cells, NK cells, etc., and also work as an adjuvant for an anticancer drug(s) by hematopoiesis enhancement effect, bone marrow defense effect, radiation sensitivity defense effect, etc., and a process for preparation of the polysaccharides by heating the leaves and/or stems of the *Panax* genus plants in water at 50-180° C. for 0.5-20 hours to extract the polysaccharides therefrom.

BACKGROUND OF THE INVENTION

20% of American deaths every year have been reported to be caused by cancer-related diseases. For treatment of these cancers, chemotherapy is usually used, but few anticancer drugs have been known to be effective.

Most of deaths caused by cancer stem from the metastasis of cancer rather than the first occurrence of cancer itself. (Fifler, 1991 cancer metastasis. Br. Med. Bull. 47, 157-177). By many experiments and clinical tests, it was confirmed that the natural immunity plays an important role in inhibiting the cancer metastasis and destroying a cancer itself (Schantz et al., cancer immunol. Immunother. 25., 141-148, 1987).

NKT (Natural Killer T) cells are a specialized population of α/β T cells that coexpress receptors of the NK lineage and have the unique potential to secrete very rapidly the large amount of cytokines providing early help for effector cells and regulating the Th1 or Th2 differentiation of some immune responses (Annu. Rev. Immunol. 1997. 15; Albert Bendelae et al. p 535). Moreover, they also eliminate infectious germs or bacteria such as cancer cells, parasites, listerias, tuberculoses, and so on (Seki et al., Clin. Immunol., 28, p 1069, 1996).

NK cells, LAK cells and macrophages, in addition to the NKT cells, are known to be cells that can effectively inhibit infection by cancer cells, viruses, and bacteria. More particularly, the effective activation of NK cells, LAK cells and macrophages has been known to block the cancer cell growth and its metastasis. Also, the activation of NK cells by immune stimulators has been reported to inhibit the cancer cell proliferation caused by cancer metastasis (Herberman, 1984 J. invest. Dermatol. 83, 137-140).

These anticancer, anti-metastasis and anti-virus functions of the immune system are mediated by the secretion of various kinds of cytokines, activating the immune system. Especially, gamma interferon, tumor necrosis factor-alpha, etc. are the representative cytokines associated with anticancer, anti-metastasis and anti-virus functions.

Gamma interferon, which is mainly generated by T cells, serves to control the immune reaction and also activate T and B cells, neutrophils, NK cells, and macrophages to make them attack cancer cells. Therefore, Gamma interferon is used as a treatment for chronic bone marrow leukemia and kidney cancer. Moreover, Gamma interferon has a strong inhibitory effect on DNA replication and cell proliferation, so that it is also clinically applied to not only cancer treatment but also to treat virus infection, multi-resistance bacteria and fungi infection, by suppressing the proliferation of microorganisms.

Tumor necrosis factor-alpha is mainly generated by macrophages and is involved in various immune reactions such as the inflammatory reaction, and especially shows a very strong toxicity to cancer cells. At present, TNF-alpha is on the verge of approval as a skin cancer treatment in Japan, pending clinical test results.

However, using cytokines directly for anticancer therapy brings unexpected side effects, such as an inflammatory reaction, emesis and so on. Therefore, many trials are being made to find materials that can wholly activate the immune system, rather than using only a particular cytokine.

Regretfully, few natural products are known to activate immune cells including NK cells: for example, a lectin from *Viscum coloratum* extraction, which is partially used as a substitute therapy for a cancer treatment, and polysaccharides belonging to beta-glucan series obtained from a mushroom.

Meanwhile, plants belonging to *Panax* genus (so-called, "ginseng"), as a representative tonic medicine, are usually used in the form of white ginseng, being dried at room temperature after harvest, or in the form of red ginseng, being heat-treated after harvest. Much research has been performed to characterize the ingredients and medical effects of ginseng, and the reported medical effects include, aging inhibition, anti-artherosclerosis, hyperlipidemia remedy, enhancement of liver function, elimination of irradiation side effects, immune system enhancement, anti-thrombus, increase of brain function, anti-stress, blood sugar decrease, blood pressure decrease, and anticancer effects. The major ingredients inducing these effects have been found to belong to the saponin series. Recent research has focused on extraction/separation of acidic polysaccharides from the roots of ginseng so as to identify their effects. These acidic polysaccharides have been known to activate macrophages, thereby making the macrophages expedite the generation of interferon-gamma and thus inhibiting proliferation of cancer cells (Korean Patent No. 144130).

Most research so far has concentrated only on the roots of ginseng, but not on the leaves and stems of ginseng, except in some cases. While the roots of ginseng must be cultivated at least 6 years so as to exhibit a medicinal effect, the leaves and stems of ginseng are grown every year and then wasted. Accordingly, if it is found that the leaves or stems of ginseng contain specific physiologically active ingredients as the ginseng roots do, it will be a great merit in view of the use of by-products and environmental care.

As mentioned above, use of the leaves and stems of ginseng has been limited to some cases: the production of cosmetics by using saponin of ginseng leaves (Korean Patent Laid-open No. 81-3736), the method of obtaining aglycon saponin from ginseng leaves under alkali conditions (Korean Pharmaceutical Bulletin, 38(4), 1994, 8), the preparation of a shampoo and lotion by using extracts of herbs including ginseng leaves (Korean Patent No. 23641), and the preparation of a clean tissue for women containing ginseng leaves (Korean Patent No. 214223).

Some research has shown that the polysaccharides obtained from the leaves of ginseng are effective for gastric ulcer treatment (Planta Med. 58, 1992, 445-448); however, no research suggests that the extract from the leaves or stems of ginseng has an anticancer effect, cancer metastasis inhibition, etc.

SUMMARY OF THE INVENTION

The inventors of the present invention are the first to find that the extract from the leaves and/or stems of ginseng activates immune cells, such as NKT cells, NK cells, macrophages, etc., and promotes the secretion of cytokines, such as interferon-alpha, tumor necrosis factor-alpha, etc., to suppress the growth and metastasis of cancer cells and support the hematopoiesis acceleration effect and also reduce the side effects of the existing anticancer drugs and radiation treatment. The present invention was accomplished on the basis of these findings.

Accordingly, an object of the present invention is to provide an extract, obtained from the leaves and/or stems of ginseng, which has a cancer inhibition effect, a hematopoiesis enhancement effect, a bone marrow defense effect, a radiation sensitivity defense effect, etc.

Another object of the present invention is to provide a composition containing the above extract as an active ingredient.

A further object of the present invention is to provide novel uses of the above composition, such as an anticancer drug, a cancer metastasis inhibitor, a hematopoiesis enhancer, a radiation side effect inhibitor, an anticancer drug side effect inhibitor, an auto-immune disease treatment, etc.

Another object of the present invention is to provide a process of obtaining the above extract from the leaves and/or stems of ginseng.

The composition according to the present invention contains an extract as an active ingredient, which can be obtained by treating the leaves and/or stems of plants belonging to the *Panax* genus (hereinafter, referred to as "*Panax* genus plants" or sometimes as "ginseng") under special conditions. These *Panax* genus plants used in the present invention include, for example, *Panax ginseng* C. A. Mayer, *Panax quinquefolum, Panax notoginseng, Panax pseudoginseng, Panax japonicum, Panax vietnamensis* Ha et Grushv. etc., of which one or more can be used in the present invention.

The form of the composition according to the present invention is not particularly limited so far as the effect of the above extract can be exhibited, and includes, for example, a solid phase, suspension phase, emulsion phase, liquid phase and so on. Also, the amount of the above extract in the composition is not particularly limited so far as it functions as an active ingredient for the particular purpose.

In below, the present invention will be described in more detail.

In accordance with the present invention, in order to obtain an extract from the leaves and/or stems of *Panax* genus plants, these leaves and/or stems are first heated in 10-20 equivalents of water at pH 4-10, 50-180° C. for 0.5-20 hours. As mentioned above, the *Panax* genus plants to be used can be one or more of *Panax ginseng* C. A. Mayer, *Panax quinquefolum, Panax notoginseng, Panax pseudoginseng, Panax japonicum,* and *Panax vietnamensis* Ha et Grushv. etc. After this hydrothermal treatment, the leaves and/or stems of ginseng and remnants are removed by a filtering. Small, floating particles are removed by a fine filtering process and centrifugation. The final filtering process may be done with a 0.45 μm pore filter or ultrafilter and the centrifuge process may be done at 7000 rpm for 30 minutes. A solution obtained thus is concentrated, for example, by evaporation to facilitate the separation of polysaccharides therefrom. The concentration process may be carried out at 70° C., 760 mmHg, until the concentration of solution reaches 20 brix, when measured with a sugar refractometer. To effectively collect the polysaccharides from the concentrated solution, 0.1-1 M NaCl, preferably 0.5-1 M NaCl is added to the concentrated solution. Then, the polysaccharides are precipitated using alcohol, such as methanol and ethanol, propanol or acetone at 1-4 volumes, preferably 2-4 volumes. The precipitated polysaccharides are washed several times with the 95% or more alcohol or acetone to remove water and impurities, and then salts and alcohols are removed by performing dialysis or ultrafiltration. The polysaccharides obtained thus are dried by one of hot air drying, vacuum drying, freeze drying, spray drying, etc.

A refining process can be more efficiently chosen depending upon the type of target drug and its use. An exemplary process is described in below. After completion of the separation and filtration, the solution is adjusted to about pH 8.0 and 0.4 M NaCl/10 mM Tris-HCl and then loaded in an anion exchange resin column at the rate of 30 ml/min. The anion exchange resin must be previously equilibrated with 0.4 M NaCl/10 mM Tris-HCl so as to adsorb only coloring materials and impurities but not polysaccharides. The anion exchange resin column is sufficiently washed with a buffer solution. The solution, having been passed through the column, is adjusted to about pH 6-7 and then loaded in an adsorbent resin column at the rate of 30-50 ml/min. The column is sufficiently washed with distilled water (DW). The three-time ethanol precipitation method is carried out to check whether all the polysaccharides comes out the column. 3 volumes of 95% ethanol is added to the flow-through solution to efficiently precipitate only the polysaccharides, thereby concentrating the polysaccharides. To collect the polysaccharides, centrifugation (5000 rpm, 15 min) and dialysis are performed. The solution obtained thus is adjusted to pH 8. After 10 mM Tris-HCl (pH 8) buffer is added to the solution, the solution is loaded onto an anion exchange resin column at the rate of 15-20 ml/min. After the column is sufficiently washed with a buffer, elution was carried out with 0.5 M NaCl. 3 volumes of ethanol is added to the eluate to precipitate polysaccharides, and then centrifugation is performed to collect them. The collected pellet is washed two times with 95% ethanol and then dialyzed against a MW cut-off of 6000 to remove the remaining ethanol and low molecule impurities, followed by the freeze drying.

The extract obtained by solvent extraction was diluted with triple distilled water to a concentration of 1 mg/mil and then analyzed. The result showed that *Panax ginseng* C. A. Mayer has a neutral sugar content of 68.9%, an uronic acid content of 15.9%, and a protein content of 8.7%; *Panax quinquefolium* has a neutral sugar content of 57.8%, an uronic acid content of 35%, and a protein content of 5.4%.

The extract obtained by the elaborate separating/refining process using an ion exchange resin, an adsorbent resin, etc. was diluted with triple distilled water to a concentration of 1 mg/ml and then analyzed. The result showed that *Panax ginseng* C. A. Mayer has a neutral sugar content of 51.3%, an uronic acid content of 46.8%, and a protein content of 0.1%, in which the distribution of sugars was rhamnose 5.97%, fucose 1.22%, arabinose 14.86%, xylose 0.44%, mannose 1.93%, glucose 3%, galactose 22.7%, galacturonic acid 31.4%, glucuronic acid 14.4%, KDO (2-keto-3-deoxyocturosonic acid) 1.38%, and DHA (3-deoxy-D-lyxo-2-heptulosaric acid) 1.02%; *Panax quinquefolum* has a neutral sugar content of 49%, an uronic acid content of 50.8%, and a protein content of 0.2%, in which the distribution of sugars was rhamnose 9.7%, fucose 4.1%, arabinose 8.7%, xylose 0.7%, mannose 1.5%, glucose 1.2%, galactose 12%, galacturonic acid 44%, glucuronic acid 5%, KDO 6%, and DHA 1.2%.

It was found by the inventor of the present invention that the extract from the leaves and/or stems of ginseng has a molecular weight of approximately 6,000-340,000 Da, and an average molecular weight of around 120,000 Da.

Also, the composition of sugar was varied depending upon the kind of ginseng, like 30-80% in the case of neutral sugar, 10-60% in the case of acidic sugar, and 0.01-10% in the case of protein; however, the sugars commonly comprised rhamnose, fucose, arabinose, xylose, mannose, glucose, galactose, galacturonic acid, glucuronic acid, KDO and DHA, and all the extracts exhibited the effect of anticancer, anti-metastasis, and/or anticancer drug adjuvant.

A composition containing the extract or polysaccharides, obtained from the leaves and/or stems of ginseng as above, activates the overall immune system such as NKT cells, NK cells, macrophages, T cells, B cells, etc. and also accelerates the secretion of cytokines associated with anticancer function, thereby significantly reducing the proliferation and metastasis of cancer cells. Accordingly, the composition can be used as an anticancer drug and anticancer metastasis inhibition drug. Also, the composition can be used as an adjuvant for anticancer drugs or radiation treatment by reducing the side effects thereof.

The composition according to the present invention can be formulated by itself or with carriers, conventionally acceptable in the pharmaceutical field, in the conventional dosage form such as oral administration drugs, for example, pill, capsule, liquid form, suspension form, etc., and injection drugs. In order to prevent the drug from being degraded by the gastric acids in oral administration, it may be co-administered with antacid agents or formulated with an enteric coating.

The dosage of the polysaccharides into the human body must be properly determined by considering the absorption rate of active ingredients, the inactivation rate, the excretion rate, patient's age, gender and current condition, etc., and is generally 100 μg-6000 mg, preferably 20-5000 mg per day for adults.

The composition according the present invention may further contain an anticancer drug(s) and/or an adjuvant(s) thereof or be co-administered together them. The kind of anticancer drug is not particularly limited, and examples thereof include Taxol® and Cisplatin®.

DETAILED DESCRIPTION OF PREFERRED EMBODIMENTS

Figure 1:
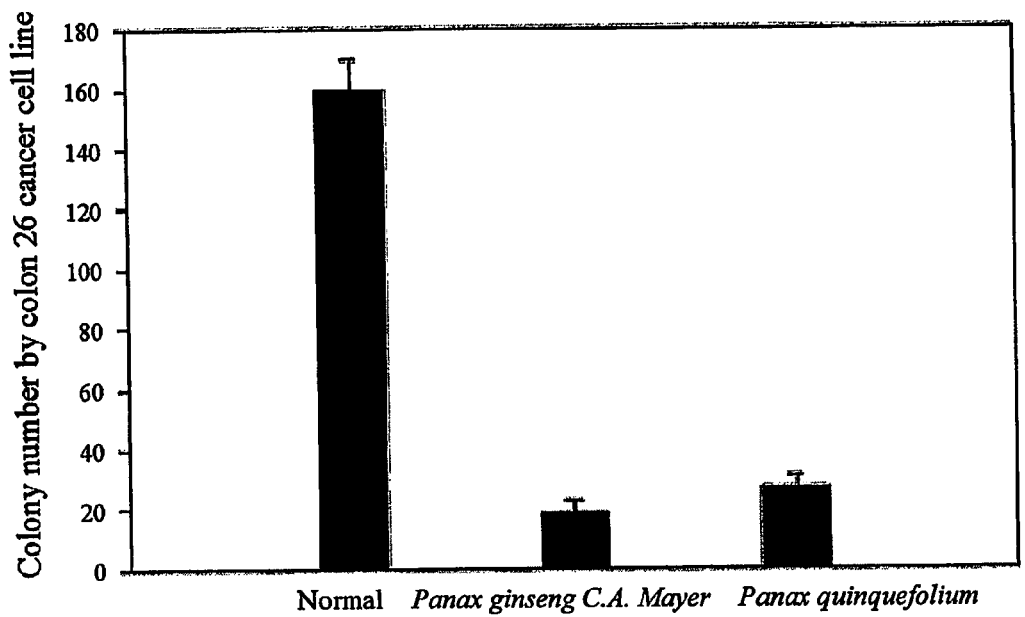
FIG. 1 is a graph showing the inhibitory effect of the polysaccharides obtained from the leaves and stems of *Panax ginseng* C. A. and *Panax quinquefolium* on the metastasis of lung cancer, in accordance with EXPERIMENTAL EXAMPLE 1 and COMPARATIVE EXAMPLE 1 of the present invention.

The present invention is described in more detail with reference to the following examples. However, the scope of the present invention is not limited to these.

Preparation Example 1

Preparation of a Crude Polysaccharide Extract from the Leaves and/or Stems of Ginseng 100 g of the *Panax ginseng* C. A. Mayer leaves and/or stems was added into 1 L of water and then heated at 100° C. for 5 hours in order to extract active ingredients therefrom. The liquid phase was separated from the leaves and/or stems by filtration and centrifuged at 7,000 rpm for 30 minutes to remove insoluble impurities therefrom. The supernatant, containing polysaccharides, was concentrated to 20 brix at 70° C. under 760 mmHg, to obtain 100 ml of the concentrated solution. Sodium chloride was added to a final concentration of 1 M, and 300 ml of ethanol was then added. The resulting mixture was left for 1 hour to allow precipitation. The precipitate was washed two times with 100 ml of 95% ethanol to remove impurities and then dialyzed, followed by freeze-drying, to obtain a crude polysaccharide extract.

The above process was also repeated for the leaves and/or stems of *Panax quinquefolium* to obtain a crude polysaccharide extract.

Preparation Example 2

Preparation of Polysaccharides from the Leaves and/or Stems of Ginseng 500 g of *Panax ginseng* C. A. Mayer was added into 5 L of distilled water and heated for 3 hours to prepare an extract solution. Slurry was separated from the extract solution by gauze. The extract solution was centrifuged at 7,000 rpm for 20 minutes to separate a supernatant. The supernatant was adjusted to about pH 8.0 and 0.4 M NaCl/10 mM Tris-HCl and then loaded in an anion exchange resin column (PA312-based strong basic anion exchange resin, Samyang Corporation) at the rate of 30 m/min. The anion exchange resin had been previously equilibrated with 0.4 M NaCl/10 mM Tris-HCl so as to adsorb only impurities and prevent polysaccharides from being adsorbed. The anion exchange resin was sufficiently washed with a buffer, and the solution, having passed through the resin, was adjusted to about pH 6-7. The resulting solution was loaded in an adsorbent resin (HP 20, Mitsubishi Corporation) at the rate of 30-50 ml/min. The column was sufficiently washed with distilled water, and then the triple ethanol precipitation method was used to confirm whether all the solution had passed through the column. 3 volumes of 95% ethanol was added to the flow-through solution to efficiently precipitate only polysaccharides, thereby concentrating the polysaccharides. In order to collect the polysaccharides, the solution was centrifuged at 5,000 rpm for 15 minutes and then dialyzed. The resulting solution, which was adjusted to pH 8, 10 mM Tris-HCl, was loaded onto an anion exchange resin column (Q sepharose, Phamacia biotech. Corporation) at the rate of 15-20 ml/min to perform adsorption. The column was washed with 10 mM Tris-HCl buffer and the elution was carried out with 0.5 M NaCl. 3 volumes of ethanol was added the solution to precipitate the polysaccharides. The solution was centrifuged at 5,000 rpm for 15 minutes to obtain a precipitant. The precipitant was washed two times with 95% ethanol to remove impurities, and dialyzed against a molecular weight cut-off of less than 6000 to remove the remaining ethanol, followed by freeze-drying, to obtain the polysaccharides.

The above process was also repeated for the leaves and/or stems of *Panax quinquefolium* to obtain polysaccharides.

Preparation Example 3

Preparation of MB40100, an Extract from the Leaves and/or Stems of Ginseng, and Preparation of a Liquid Solution for Injection The solution that had been loaded in the anion exchange resin column (Q-sepharose) in PREPARATION EXAMPLE 2, originated from *Panax ginseng* C. A. Mayer, was loaded in a column filled with silica gels to remove pyrogen materials therefrom. 3 volumes of ethanol was added to precipitate polysaccharides, and the polysaccharides were collected by centrifugation and then washed two times with 95% ethanol to remove impurities. The resulting segment was dissolved in triple distilled water and then dialyzed against a molecular weight cut off of less than 6,000 to remove the remaining ethanol. For sterility, the resulting fraction was loaded in a 0.2 µm filtering system to prepare a solution without pyrogen materials. The aseptic solution was freeze-dried in a 3 ml vial to prepare a polysaccharide fraction. The dried polysaccharide fraction was dissolved in saline solution to prepare a liquid solution for injection, which was used in EXAMPLES as below. The polysaccharides, extracted from the leaves or stems of *Panax ginseng* C. A. Mayer, was named "MB40100."

Experimental Example 1

Analysis of an Extract Obtained from the Leaves and/or Stems of Ginseng

A component analysis was performed on the extracts prepared in the above PREPARATION EXAMPLES.

The total content of sugars was measured by the phenol-sulfuric acid method (Dubois et al Anal. Chem., 28, 350, 1956) using galactose as a standard material. The content of uronic acid was measured by the m-hydroxybiphenyl method (Blumenkrantz et al, Anal. biochem., 54, 484, 1973) using β-D-galacturonic acid as a standard material. The content of protein was measured by the Lowry method (Lowry et al, J. Biol., Chem., 193, 265, 1951) using bovine albumin as a standard material. The content of KDO (3-deoxy-D-manno-2-octubsonic acid) was measured by the thiobarbituric acid method.

The analysis of polysaccharides was carried out by the gas-liquid chromatography (GLC) method, using the Jones method (plant physiol., 49, 926, 1972) with alditol acetate as derivatives.

The crude extract, obtained in PREPARATION EXAMPLE 1, was dissolved in triple distilled water to a concentration of 1 mg/ml and then analyzed according to the above methods. The results showed that *Panax ginseng* C. A. Mayer has a neutral sugar content of 68.9%, an uronic acid content of 15.9%, and a protein content of 8.7%; *Panax quinquefolium* has a neutral sugar content of 57.8%, an uronic acid content of 35%, and a protein content of 5.4%.

The extract, obtained in PREPARATION EXAMPLE 2, was dissolved in triple distilled water to a concentration of 1 mg/ml and then analyzed according to the above methods. The results showed that *Panax ginseng* C. A. Mayer has a neutral sugar content of 51.3%, an uronic acid content of 46.8%, and a protein content of 0.1%, in which its sugar composition comprises rhamnose 5.97%, fucose 1.22%, arabinose 14.86%, xylose 0.44%, mannose 1.93%, glucose 3%, galactose 22.7%, galacturonic acid 31.4%, glucuronic acid 14.4%, KDO 1.38%, and DHA (d-deoxy-D-lyxo-2-heptulosaric acid) 1.02%; *Panax quinquefolium* has a neutral sugar content of 49%, an uronic acid content of 50.8%, and a protein content of 0.2%, in which its sugar composition comprises rhamnose 9.7%, fucose 4.1%, arabinose 8.7%, xylose 0.7%, mannose 1.5%, glucose 1.2%, galactose 12%, galacturonic acid 44%, glucuronic acid 5%, KDO 6%, and DHA 1.2%.

The molecular weight was measured by HPLC with GS-520HQ, GS-320HQ and GS-220HQ (Shodex Asaipack GS series, Showa Denko Corporation) being connected in series. According to the measurement, the extract of the leaves and/or stems of ginseng has a molecular weight of about 6,000 Da-340,000 Da and an average molecular weight of around 120,000 Da.

While the polysaccharide compositions vary depending on the kind of the leaves and stems of ginseng, such as 30-80% in the case of neutral sugar, 10-60% in the case of the uronic sugar, and 0.01-10% in the case of protein, the sugar compositions have commonly rhamnose, fucose, arabinose, xylose, mannose, glucose, galactose, galacturonic acid, glucuronic acid, KDO and DHA, and in all types of the extracts, the effect of anticancer and anti-metastasis was exhibited and the function of an anticancer adjuvant was found.

Comparative Example 1

Comparison of Activities of Polysaccharides Extracted from *Panax ginseng* C. A. Mayer and *Panax quinquefolium*

The ability of each extract obtained from each PREPARATION EXAMPLE to inhibit lung cancer metastasis was measured, and it was found that *Panax ginseng* C. A. Mayer has an inhibition rate of 88.3%, while *Panax quinquefolium* has an inhibition rate of 83.1% (refer to FIG. 1). In the following EXAMPLES, MB40100, the polysaccharides extracted from *Panax ginseng* C. A. Mayer, were used because it exhibits a higher inhibition rate against cancer metastasis.

Experimental Example 2

Figure 2:
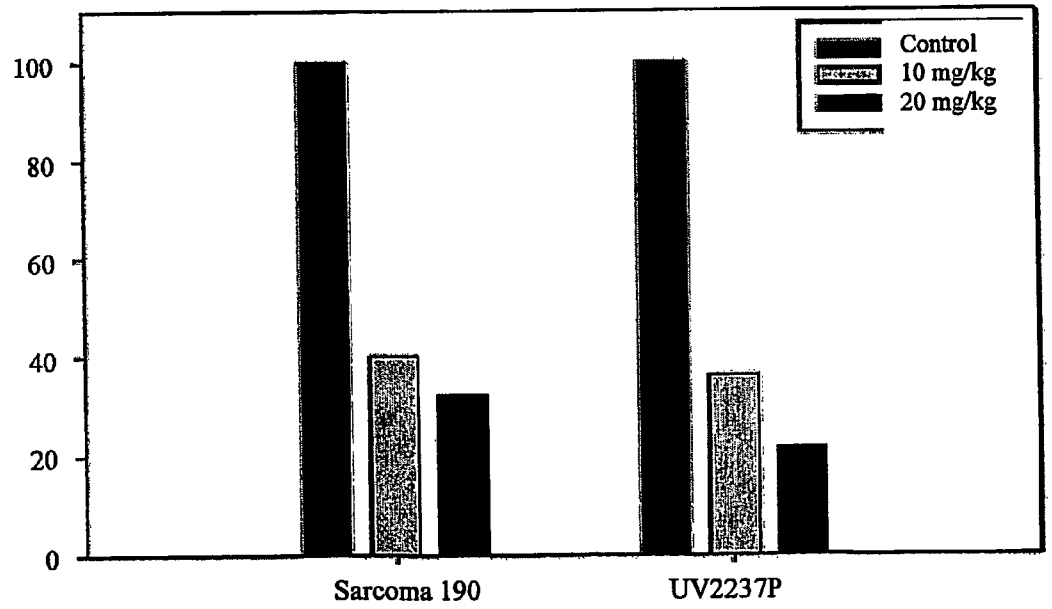
FIG. 2 is a graph showing the anticancer effect of MB40100, an extract from the leaves or stems of ginseng, on a solid cancer, in accordance with EXPERIMENTAL EXAMPLE 2 of the present invention.

Anticancer Effect of MB40100 Against Solid Cancers $1 \times 10^6$ Sarcoma 180 cells, as a non-epithelial cancer cell line, were injected in the groins of BALB/c mice (20 heads/group). 3 days after injection, MB40100 was orally administered one time a day during 10 days, at concentrations of 10 and 20 mg/kg, and after oral administration, the size of the tumors was compared with that of the control group. The above process was repeated for UV2237P cells, as an epithelial cancer cell line. As shown in FIG. 2, MB40100 treatment reduced tumor size by 60% at a dosage of 10 mg/kg, and 70% at a dosage of 20 mg/kg, in the case of non-epithelial cancer. Versus epithelial cancer, MB40100 treatment reduced tumor size by 65% and 78%, respectively, at corresponding dosage.

Experimental Example 3

Prophylactic Effect of MB40100, Versus Lung Cancer Metastasis

Figure 3:
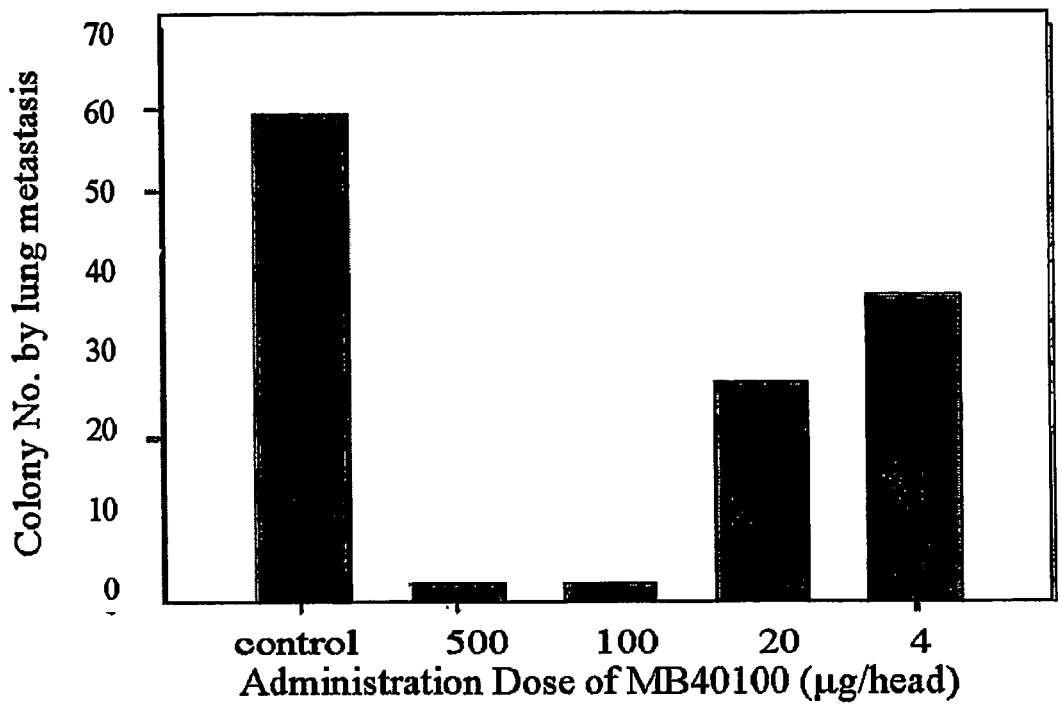
FIG. 3 is a graph showing the prophylactic effect of MB40100 on lung cancer metastasis in accordance with EXPERIMENTAL EXAMPLE 3 of the present invention.

Colon 26-M3.1 cells, as highly metastatic colon carcinoma cells, were cultured in Eagles MEM containing 7.5% FBS, vitamin solution, sodium pyruvate, non-essential amino acids and L-glutamine. The experiment for the lung cancer metastasis of colon 26-M3.1 cells was performed by injecting cancer cells into Balb/c mice and then measuring the degree of cancer metastasis (Yoo et al, 1994 Vaccine 12, 175-180). MB40100, dissolved in PBS and filtered by a 0.2 µl aseptic filter paper, was injected into veins of each mouse at different dosages, i.e., 500 µg, 100 µg, 20 µg, and 4 µg, respectively. 2 days after injection, the colon 26-M3.1 cells ($2.5 \times 10^4$ cells/mouse) were injected to evaluate the prophylactic effect against cancer metastasis. 14 days after injection, the mice were killed and their lungs were preserved in Bouin's solution. The number of cancer cells metastasized to the lung was counted. As shown in FIG. 3, MB40100, injected in the blood vessel, significantly inhibited the lung metastasis of colon 26-M3.1 cell.

Experimental Example 4

Therapeutic Effect of MB40100 on Lung Cancer Metastasis

Figure 4:
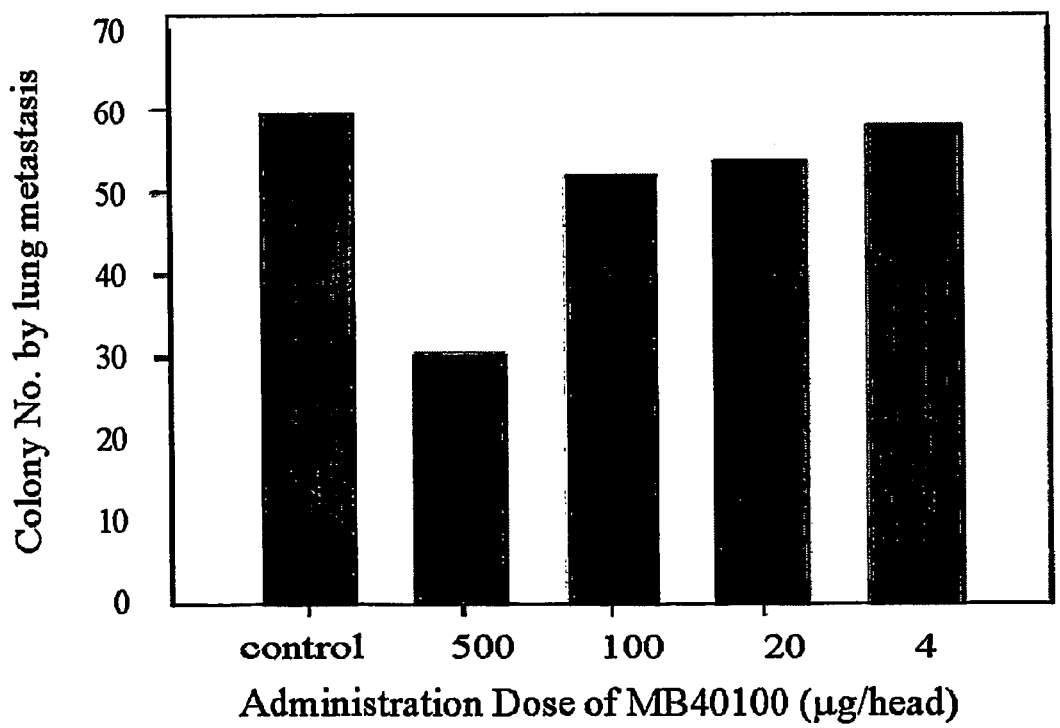
FIG. 4 is a graph showing the effect of MB40100 on reduction of lung cancer metastasis in accordance with EXPERIMENTAL EXAMPLE 4 of the present invention.

Colon 26-M3.1 cells, as highly metastatic colon carcinoma cells, were cultured in Eagles MEM containing 7.5% FBS, vitamin solution, sodium pyruvate, non-essential amino acids and L-glutamine. The experiment for the lung cancer metastasis of colon 26-M3.1 cells was performed by injecting cancer cells into C57BL/6 mice and Balb/c mice, respectively, to measure the degree of cancer metastasis (Yoo et al, 1994 Vaccine 12, 175-180). MB40100, dissolved in PBS and filtered by a 0.2 µl aseptic filter paper, was injected into each mouse at different dosages. The colon 26-M3.1 cells ($2.5 \times 10^4$ cells/mouse) were injected into mice to induce the growth of the metastasized cancers. 1 and 4 days after injection, respectively, 500 µg, 100 µg and 20 µg of MB40100 were injected into the blood vessels of mice, respectively, to measure the therapeutic effect on cancer metastasis. 14 days after injection of cancer cells, the mice were killed and their lungs were separated and preserved in Bouin's solution. The number of cancer cells metastasized to the lung was counted through microscopy. As shown in FIG. 4, MB40100, injected in the blood vessel, significantly inhibited the growth of colon 26-M3.1 cell metastasized in lung cells, depending upon administration dosage.

Experimental Example 5

Measurement of the NK-Mediated Cytotoxicity to Cancer Cells, Activated by MB40100

The NK-mediated cytotoxicity to cancer cells, activated by MB40100, was evaluated by measuring the activity of $^{51}$Cr, a radioactive isotope (Yoo et al, 1997, Jpn. J. Cancer Res. 88, 184-190). 500 µg, 100 µg, 20 µg, and 4 µg of MB40100 were injected into the veins of two Balb/c mice per group, respectively. 2 days after injection, the splenocytes of mice were harvested. $^{51}$Cr-labelled Yac-1 cells ($1 \times 10^4$/100 µl/well) were put into each splenocyte solution in a round-bottomed 96-well plate at the ratio (E/T ratio) of effector (splenocytes): target (Yac-1) cell of 100:1, 50:1, 25:1, and 12.5:1, respectively. They were cultivated under the condition of 5% $CO_2$ and 37° C. for 6 hours. After cultivation, the plate was centrifuged for 10 minutes, and then a supernatant in each well was absorbed by a cotton swab. The amount of the radioactive isotope was measured using a gamma counter. The cytotoxicity generated by NK cells was calculated as radioactivity (count/min) according to the following formula:

Cytotoxicity(%)=[(experimental release−spontaneous release)/(maximum release−spontaneous release)]×100

Figure 5:
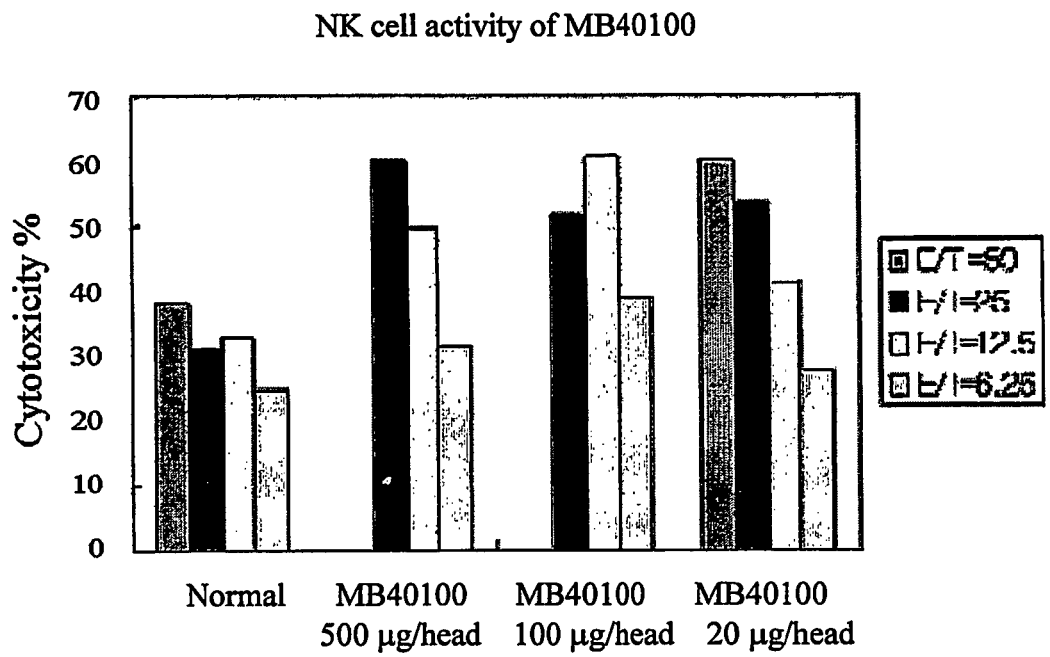
FIG. 5 is a graph showing the enhancement of NK cell-mediated cytotoxicity to cancer cells, by MB40100, in accordance with EXPERIMENTAL EXAMPLE 5 of the present invention.

As seen in FIG. 5, the activity of NK cells in the splenocytes of mice, having been injected with MB40100, increased depending upon the concentration of MB40100, and groups administered with 500 µg, 100 µg and 20 µg showed activity increases of 3-10 times, compared with the control group. While the activity of NK cells usually varies somewhat with the E/T ratio, the activity of NK cells in the present experimental example significantly increased, regardless of the E/T ratio.

Experimental Example 6

Enhancement of Hematopoiesis Function by Generation of Granulocyte Macrophage-Colony Forming Unit (GM-CFU)

Bone marrow cells at $1 \times 10^5$ cell/ml were put into a 35 mm petri dish (with 2 mm grid, Nalgen Nunc), treated with MB40100 at different concentrations, using 1 ml of MethoCult (Stem Cell, Canada) agar, and then cultivated in an incubator under the condition of 37° C. and 5% $CO_2$ for 7 days.

Figure 6:
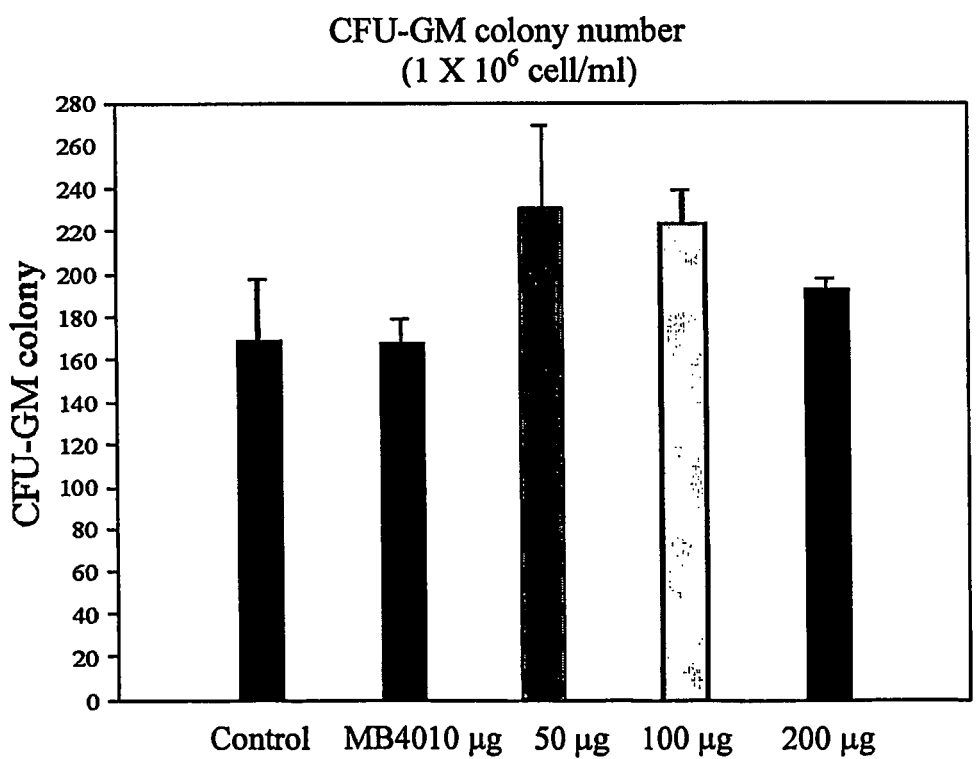
FIG. 6 is a graph showing the increase of the granulocytes macrophage-colony forming unit (GM-CFU) induced by an extract from the leaves or stems of ginseng, in accordance with EXPERIMENTAL EXAMPLE 6.

Agar without MB40100 was used for the control group. After cultivation for 7 days, the cultivated 35 mm petri dish was put on a 60 mm petri dish with a 2 mm grid and the number of colonies was counted through microscopy. While the number of colonies in the 10 μg-treated group was 168, which is not different from that in the non-treated control group, the number of colonies in the 50 μg and 100 μg-treated group increased 36.6% and 32.5%, respectively, compared to the control group (refer to FIG. 6).

Experimental Example 7

Effect of MB40100 to Reduce Level of Hematopoiesis Inhibition Caused by Anticancer Drugs Generally, anticancer drugs (e.g. cyclophosphamide) work as an immune inhibitor in vivo, thereby decreasing the number of cells in the immune system, which is a representative side effect of anticancer drugs. In the present experiment, the number of immune cells was measured in co-administration of MB40100, which was expected to reduce the immune inhibition occurring with administration of cyclophosphamide.

24 hours and 48 hours after administration of cyclophosphamide (250 mg/kg), MB40100 was abdominally administered in mice at the different dosages (10 mg/kg, 20 mg/kg), respectively. After 7 days, the mice were killed to separate bone marrow cells and splenocytes, and then the number of these cells was counted pursuant to the tryphan blue exclusion method.

Peripheral blood was rapidly gathered from the eyeball distal vein using a heparin-treated capillary glass tube and collected in a K3-EDTA-treated blood-gathering tube, then examined it with an automatic globule analyzer.

A. Variation of the Number of Leukocytes (White Blood Cell: WBC) after Administration of Cyclophosphamide When measured using the automatic globule analyzer, the number of WBC in blood, gathered from the eyeball distal vein of the normal mouse, was 7800 on the average; however, the number of WBC in the cyclophosphamide-administered mice group was 5300, which is reduced by about 30% compared that of the normal mouse. Meanwhile, in a mice group where 10 mg/kg and 20 mg/kg of MB40100 were administered 2 days before administration of cyclophosphamide, the number of WBC was 6600 and 6400, respectively, which is around 15% higher compared with that of mice administered with cyclophosphamide alone.

Figure 7:
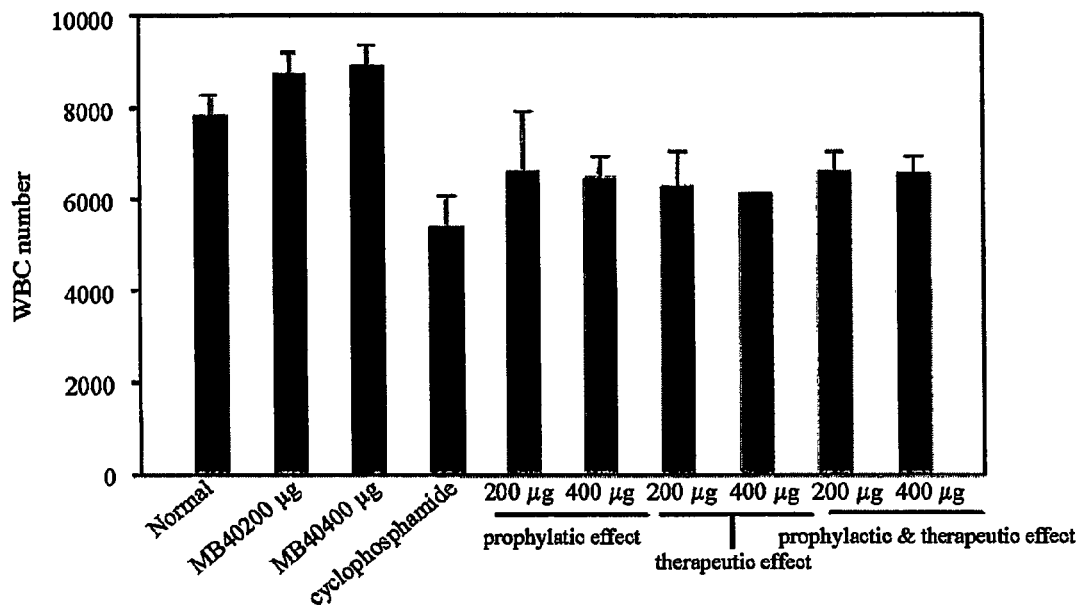
FIG. 7 is a graph showing the effect of reducing the anticancer drug-induced hematopoiesis inhibition by MB40100 in accordance with EXPERIMENTAL EXAMPLE 7, which is represented as the variation of the number of leucocytes in blood.

Furthermore, in a mice group where MB40100 was administered 1 day after administration of cyclophosphamide, the number of WBC also was about 12.1% higher than in the control group; however, there were no differences depending upon the concentration of MB40100. Also, in a mice group where MB40100 was administered two times before and after administration of cyclophosphamide, the number of WBC was about 15% higher than in the control group (refer to FIG. 7).

B. Variation of the Number of Thrombocytes in Peripheral Blood

Figure 8:
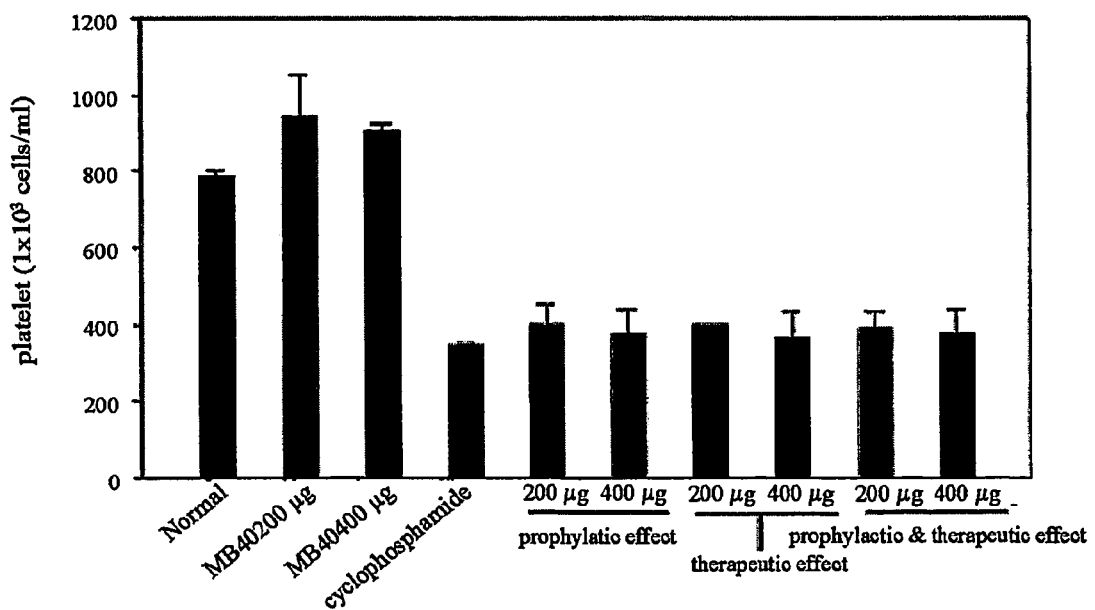
FIG. 8 is a graph showing the effect of reducing the anticancer drug-induced hematopoiesis inhibition by MB40100 in accordance with EXPERIMENTAL EXAMPLE 7, which is represented as the variation of the number of platelets in blood.

The number of thrombocytes in mice to which cyclophosphamide was administered alone was about 56% less than that of a normal mouse. When MB40100 was administered, the number of thrombocytes was about 6.6% higher than when cyclophosphamide was administered alone, which shows the recovery effect. Moreover, the increase was about 6-7% regardless of administering MB40100 before or after administration of cyclophosphamide (refer to FIG. 8).

C. Variation of the Number of Splenocytes

Figure 9:
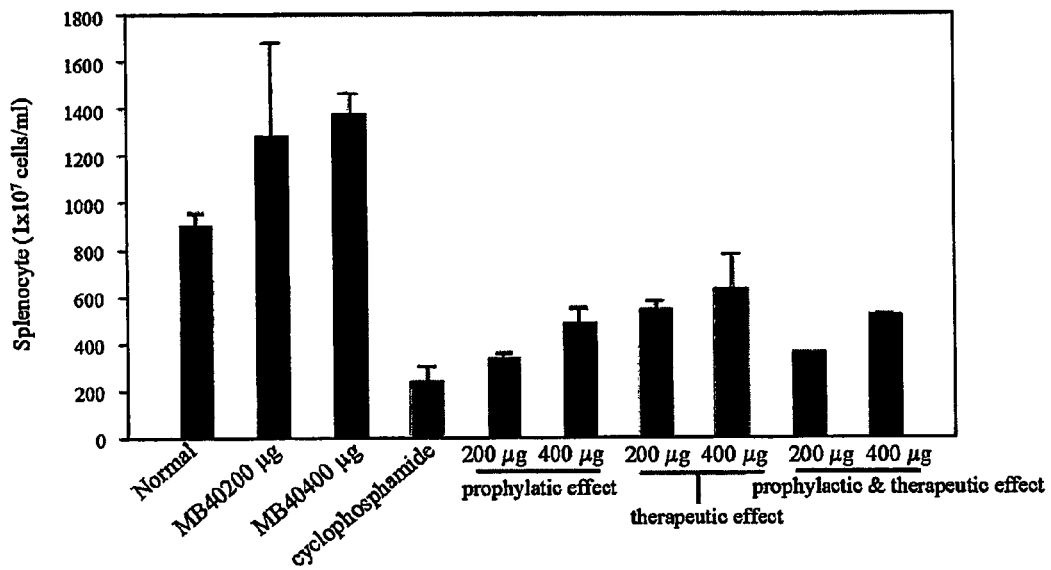
FIG. 9 is a graph showing the effect of reducing the anticancer drug-induced hematopoiesis inhibition by MB40100 in accordance with EXPERIMENTAL EXAMPLE 7, which is represented as the variation of the number of splenocytes.

The number of splenocytes in mice to which cyclophosphamide was administered alone was about 72.8% less than that of a normal mouse. Meanwhile, when 20 mg/kg of MB40100 was administered before administration of cyclophosphamide, the number of splenocytes was 26.8% higher than that of the mice with cyclophosphamide administered alone. Also, in a mice group where 10 mg/kg and 20 mg/kg of MB40100 were administered after administration of cyclophosphamide, respectively, the number of splenocytes was 33% and 43% higher. The above result shows that MB40100 can reduce the immune cell inhibition caused by anticancer drugs (refer to FIG. 9).

Figure 10:
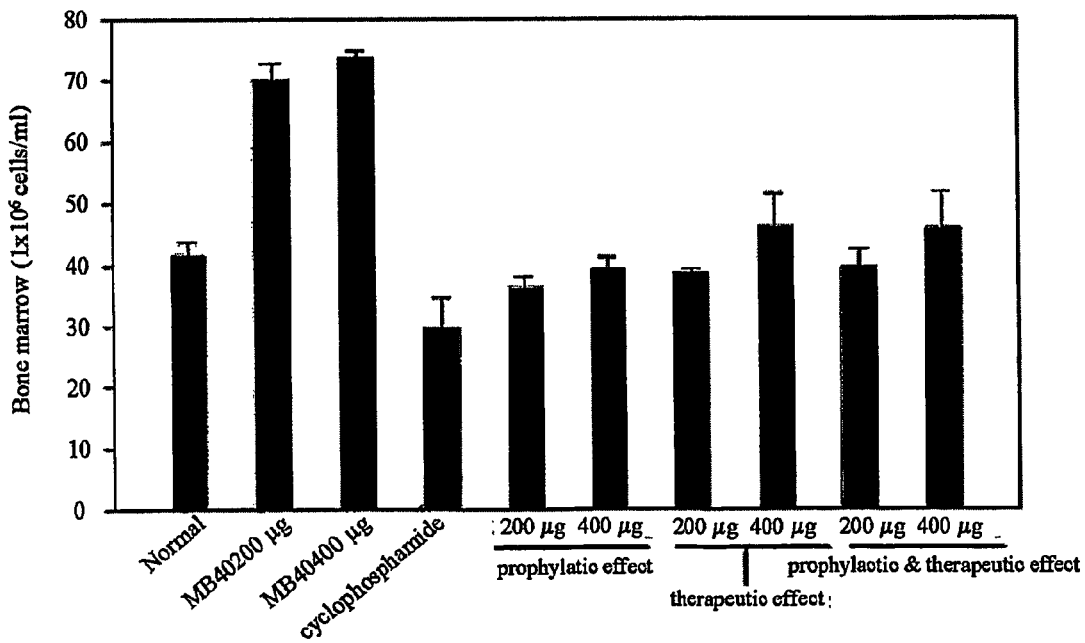
FIG. 10 is a graph showing the effect of reducing the anticancer drug-induced hematopoiesis inhibition by MB40100 in accordance with EXPERIMENTAL EXAMPLE 7, which is represented as the variation of the number of bone marrow cells.

D. Variation of the Number of Bone Marrow Cells 7 days after administration of cyclophosphamide, the bone marrow cells of the killed mice were counted. The bone marrow cell density of a normal mouse were $41.1 \times 10^6$ cells/ml, but the bone marrow cell density of the mice administered with cyclophosphamide was $29.6 \times 10^6$ cells/ml, which is a decrease of 29.2% by the anticancer drug. However, in a mice group where 10 mg/kg and 20 mg/kg of MB40100 were administered 2 days before administration of cyclophosphamide, the number of cells was 17.1% and 18.1% higher, respectively, compared with that of the cyclophosphamide-administered mice group. Also, in a mice group where 20 mg/kg of MB40100 was administered after administration of cyclophosphamide, the number of cells was 10.78% higher (refer to FIG. 10).

Experimental Example 8

Defense Effect of MB40100 Against Radiation

Radiation therapy, often accompanying administration of anticancer drugs in the treatment of cancer, destroys bone marrow cells and has a negative effect on the generation and replication of normal immune cells, thereby deteriorating the function of hematopoiesis and immunization. In the present experiment, it was examined whether the co-administration of MB40100 can reduce the deterioration of hematopoiesis and immune functions accompanying radiation treatment.

MB40100 was abdominally administered to male Balb/c mice weighing 18-22 g and, after 48 hours, the mice were exposed to 4.5 Gy of cobalt (60Co) gamma, a semi-lethal amount. 5 and 9 days after irradiation, irrespectively, the mice were killed to harvest bone marrow cells and splenocytes, then the number of each cells were counted pursuant to Tryphan blue exclusion method. To the control group, PBS instead of MB40100 was administered.

Figure 11:
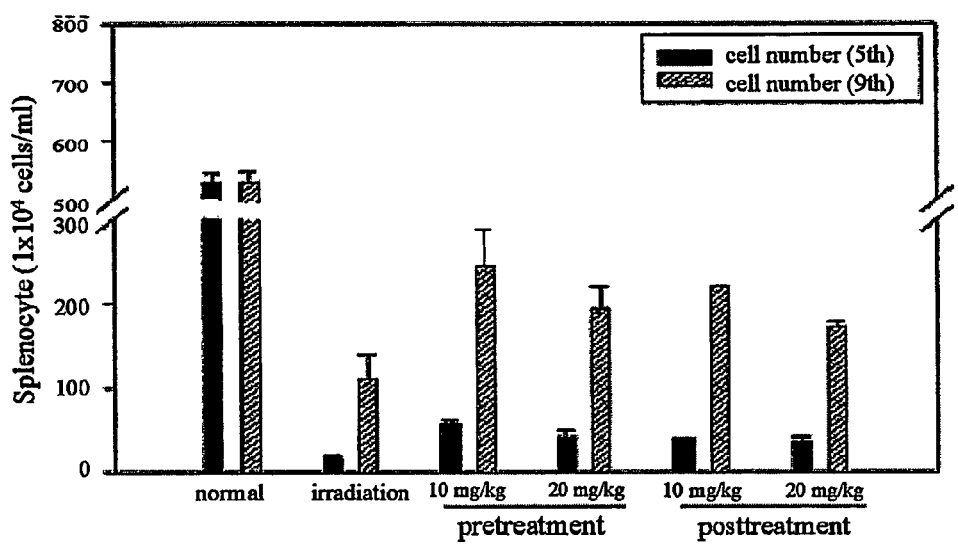
FIG. 11 is a graph showing the defense effect against radiation by MB40100 in accordance with EXPERIMENTAL EXAMPLE 8, which is represented as the variation of the number of splenocytes.

A. Variation of the Number of Splenocytes 4.5 Gy of cobalt gamma, a semi-lethal irradiation amount, was irradiated to a normal mouse and, after 5 days, the splenocytes numbered $15.8 \times 10^4$ cells/ml, which is only 3% of the splenocytes numbers of a normal mouse, and, after 9 days, had recovered to 14.8%. However, in a mice group where 10 mg/kg of MB40100 was administered 2 days before the irradiation, the number of splenocytes was 7.6% after 5 days and had recovered to 18.2% after 9 days. In a mice group where 20 mg/kg of MB40100 was administered 2 days before the irradiation, the number of splenocytes was 4.6% after 5 days, which is less than that of the 10 mg/kg-administered group, and increased no further after 9 days. Also, in a mice group where MB40100 was administered 1 day after irradiation, the number of splenocytes increased, and there were no differences depending upon the concentration of MB40100. In a mice group where MB40100 was administered before and after irradiation, the number of splenocytes increased, compared with the mice group not administered with MB40100 (refer to FIG. 11).

Figure 12:
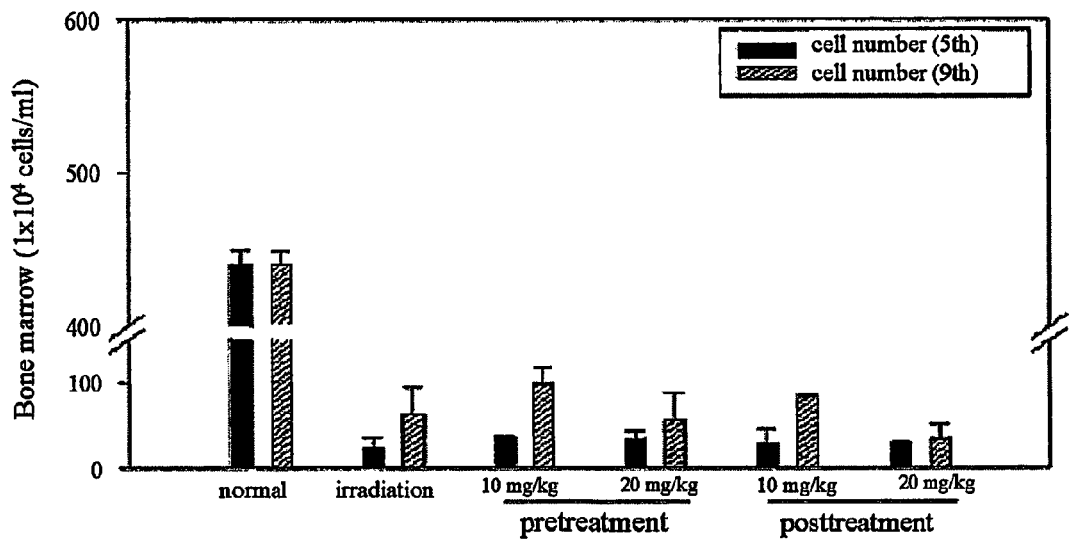
FIG. 12 is a graph showing the defense effect against radiation by MB40100 in accordance with EXPERIMENTAL EXAMPLE 8, which is represented as the variation of the number of bone marrow cells.
Figure 13A:
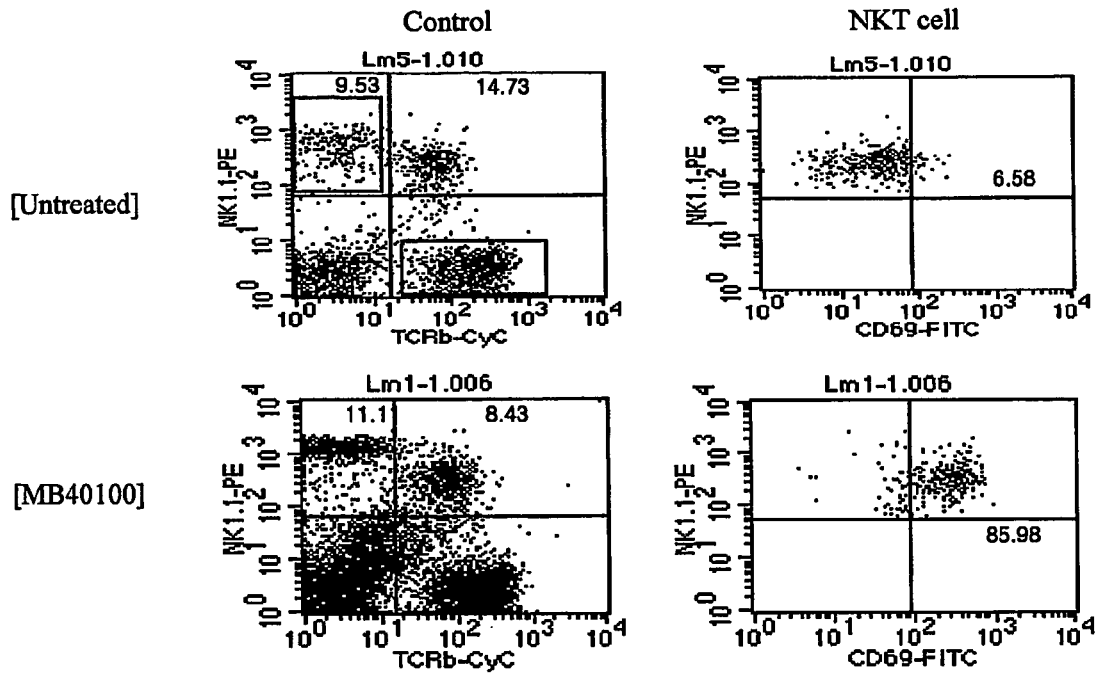
FIG. 13A to 13D are graphs showing the degree of activation of immune cells by MB40100 in accordance with EXPERIMENTAL EXAMPLE 9.
Figure 13B:
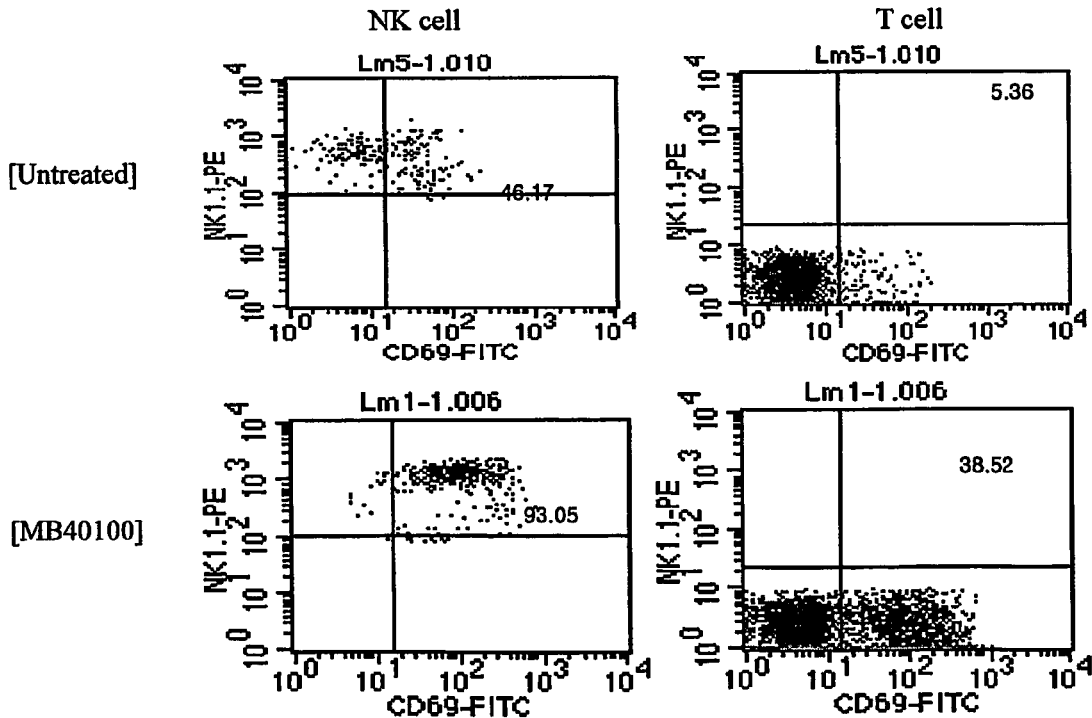
Figure 13C:
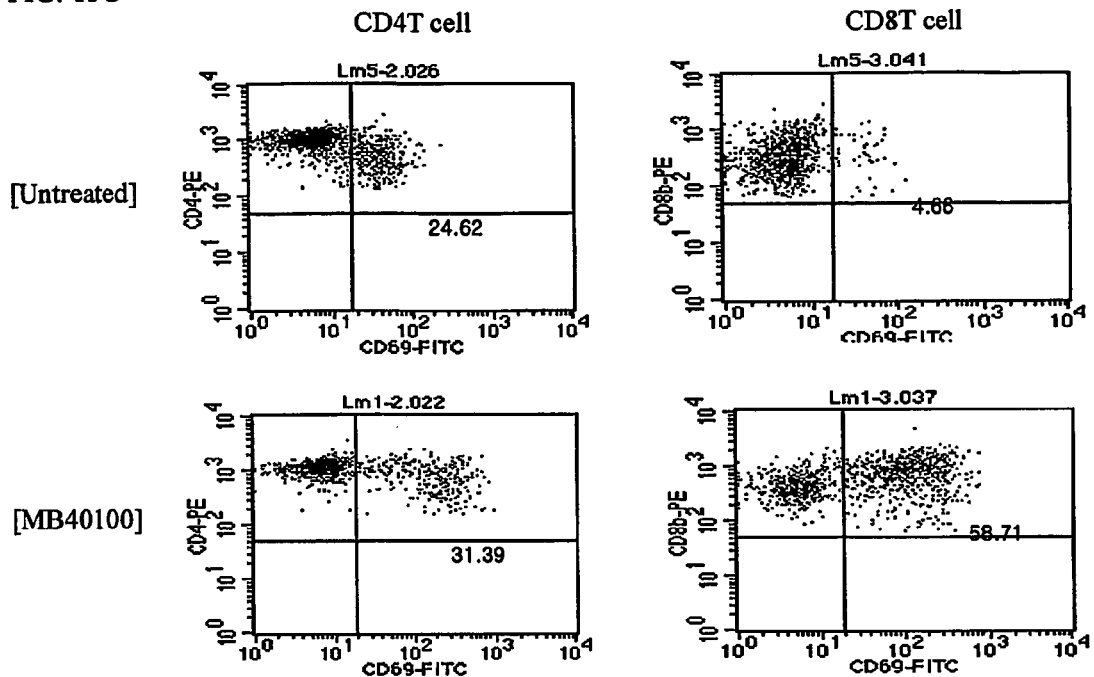
Figure 13D:
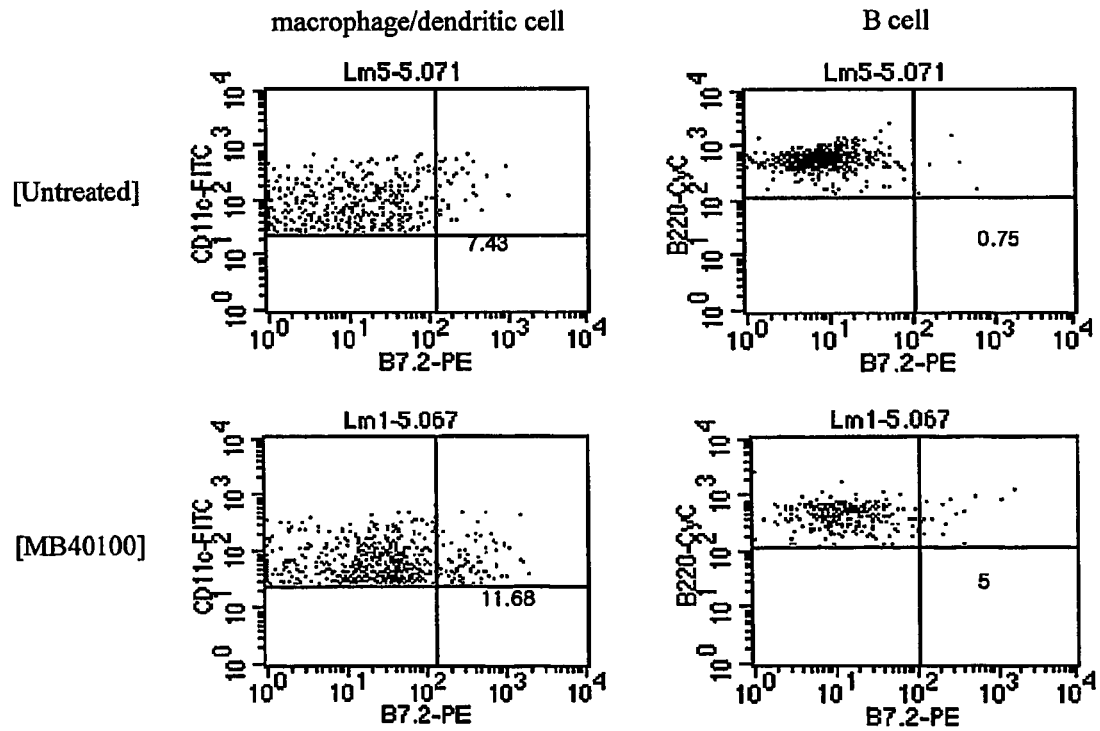

B. Variation of the Number of Bone Marrow Cells 5 days after irradiation, when bone marrow cells were collected from the left femoral region of mice, the number of cells was 5.3% of that of a normal mouse. 9 days after irradiation, the number of cells increased to 11.8% of that of a normal mouse. However, in a mice group where 10 mg/kg and 20 mg/kg of MB40100 were administered before and after irradiation, the number of cells was 6-7% higher in the mice killed after 5 days and about 15.7% higher in the mice killed after 9 days, compared to the untreated mice. Accordingly, MB40100 was confirmed to assist in protecting the bone marrow cells of the irradiated mice, thereby maintaining the hematopoiesis function (refer to FIG. 12).

Experimental Example 9

Activation of Immune Cells and Generation of Anticancer Cytokines

MB40100 was abdominally administered to C57/BL6 mice at the concentration of 10 mg/kg, and then splenocytes were harvested every hour. FACS analysis was performed on the immune cells using fluorescent-labeled receptors. The result showed that all cells associated with immunity, such as NKT cells, NK cells, dendritic cells, macrophages, CD4, CD8 cells, B cells, etc., were activated and the maximum activation occurred about 16 hours after administration of MB40100.

Figure 14A:
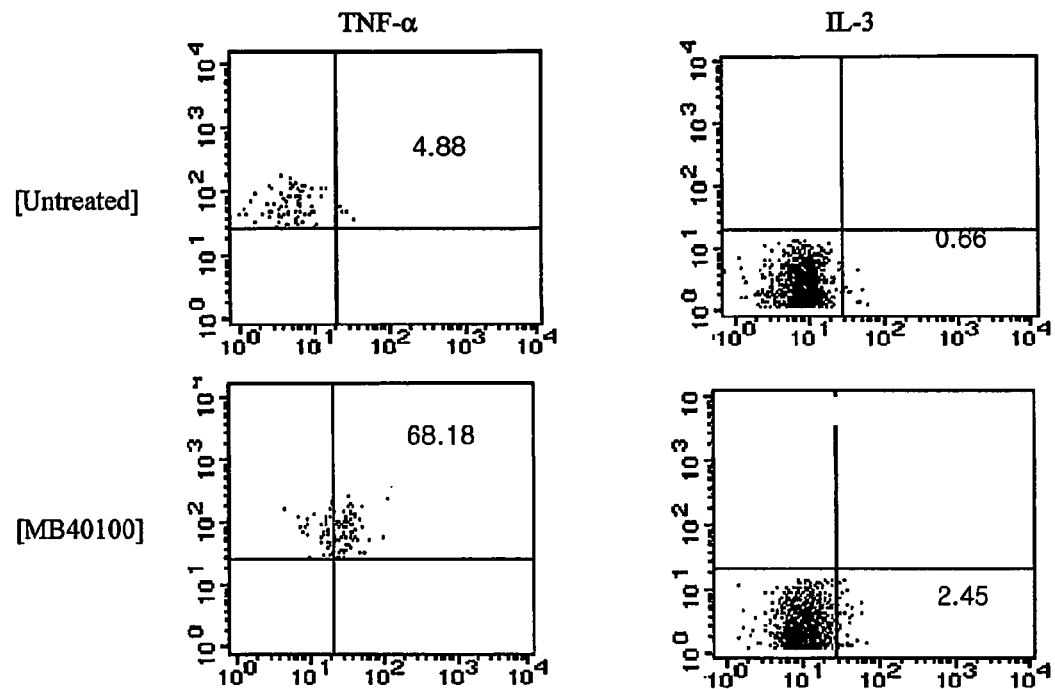
FIGS. 14A and 14B are graphs showing the level of anticancer cytokines induced by MB40100 in accordance with EXPERIMENTAL EXAMPLE 9.
Figure 14B:
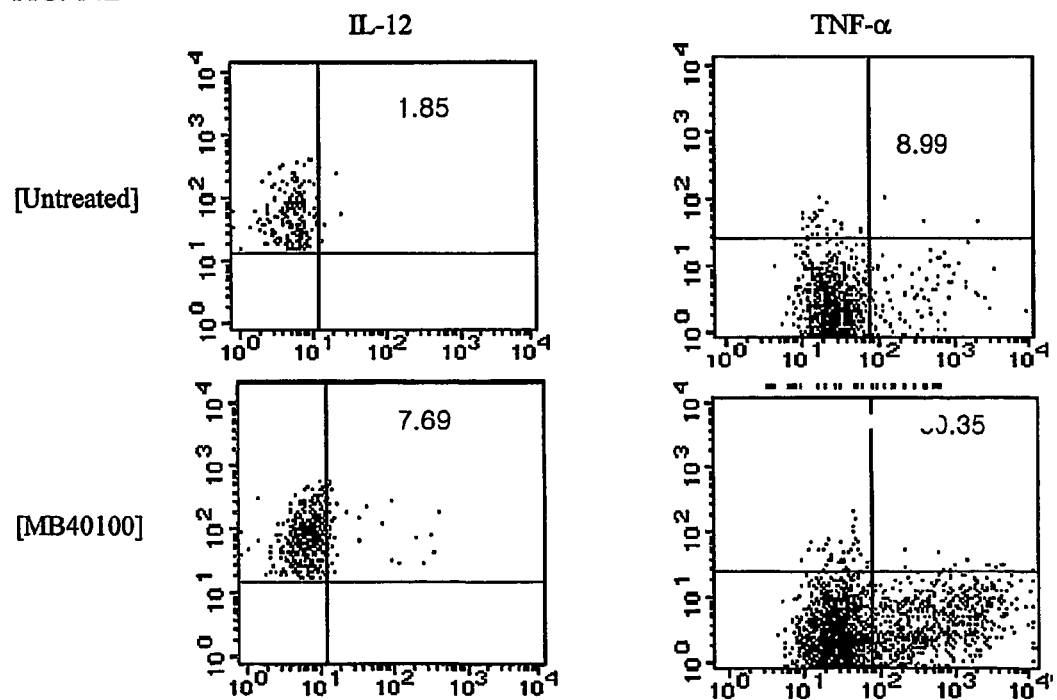

In order to measure the amount of cytokine secreted from each immune cell, MB40100 was abdominally administered to C57/BL6 mice at a concentration of 10 mg/kg and, after 16 hours, splenocytes were harvested. The amount of cytokine secreted from each immune cell, was measured using a fluorescent-labeled receptor to each immune cell and a cytokine antibody pursuant to the intracellular staining method. The result showed that, in a mice group where MB40100 was administered, TNF-a IL-3 secreted from NKT cells and T cells increased, and IL-12 and TNF-a secreted from macrophages and dendritic cells also increased (refer to FIG. 14).

Experimental Example 10

Synergistic Effect of MB40100 Co-Administered with Anticancer Drug (1)

Figure 15:
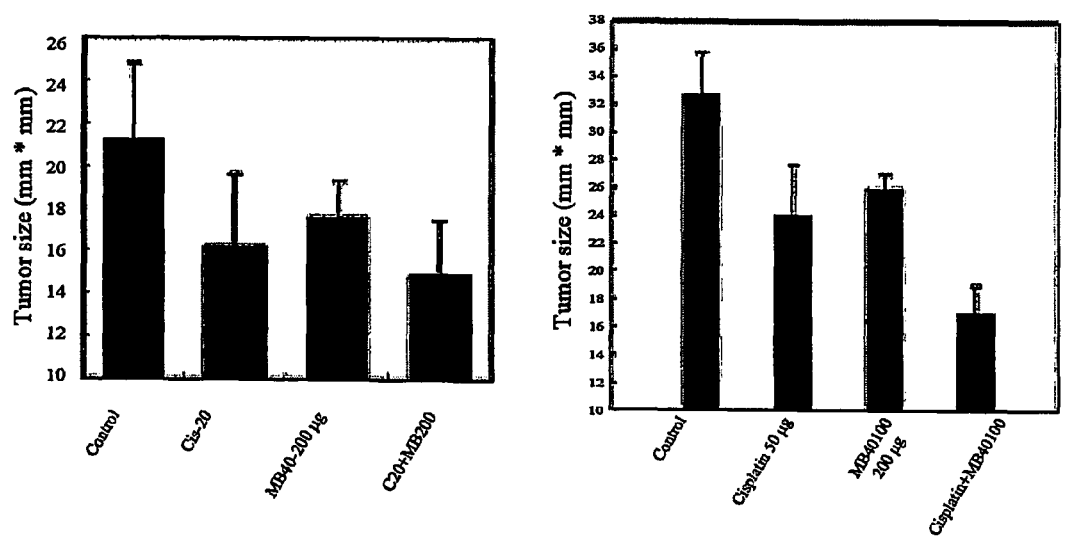
FIG. 15 is a graph showing the inhibition effect on the side effects of anticancer drug in co-administration of anticancer drug and MB40100, by MB40100 in accordance with EXPERIMENTAL EXAMPLE 10.
Figure 16:
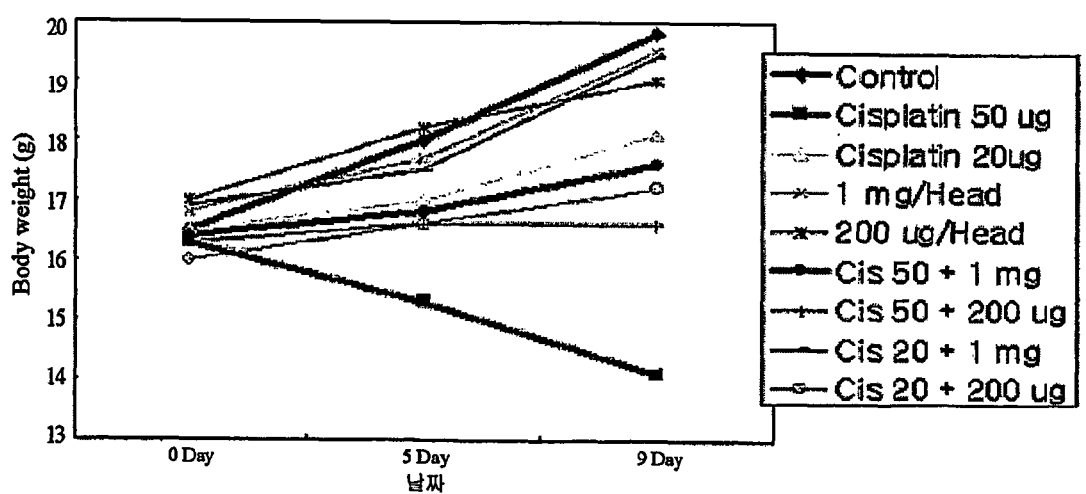
FIG. 16 is a graph showing the increase of anticancer effect by co-administration of an anticancer drug and MB40100 in accordance with EXPERIMENTAL EXAMPLE 10.

Cancer cell line B16-BL16 was intradermally injected to C57BL/6 mice in the amount of $1 \times 10^5$ cells per mouse. MB40100, filtered by 0.2 μm filter, was intravenously injected 4 times at intervals of 3 days, from 1 day after injection of cancer cells, at concentrations of 1 mg and 200 μg per mouse. Cisplatin, an anticancer drug, was intravenously injected at concentrations of 100 μg, 50 μg and 20 μg per mouse, respectively. The mice were divided into a mice group where an anticancer drug was administered alone, and a group where MB40100 was co-administered together with the anticancer drug, and the tumor size and weight were measured. The results showed that the cancer cell proliferation was inhibited by about 43% in the co-administered mice group. That is, in a mice group where MB40100 was co-administered together with Cisplatin, the mice moved actively and recovered to the weight of a normal mouse. To the contrary, in a mice group where 50 μg of Cisplatin was administered alone, serious side effects were observed, such as the loss of body weight and the decrease of mobility. As a result, M140100 is deemed to contribute the stimulation of hematopoiesis system and the activation of the immune response (refer to FIGS. 15 & 16).

Experimental Example 11

Synergistic Effect of MB40100 Co-Administered with Anticancer Drug (2)

Athymic nude mice (male) were used as an experimental subject. Tumor sizes were measured in a mice group where an anticancer drug (Taxol) was administered, a mice group where MB40100 was administered, and a mice group where Taxol and MB40100 were co-administered. Considering the condition of mice and toxicity, Toxol was administered 7 times at intervals of 3 days, from 6 days after injection of tumor, at the concentration of 12.5 mg/kg. MB40100 was abdominally administered at the concentration of 10 mg/kg, one time 2 days before injection of tumor, and at intervals of 3 days after injection of tumor, without overlapping with the days of Taxol administration. The used cancer cell line was PC-3 and hypodermically injected at an amount of $2 \times 10^6$ cells per mouse.

Figure 17:
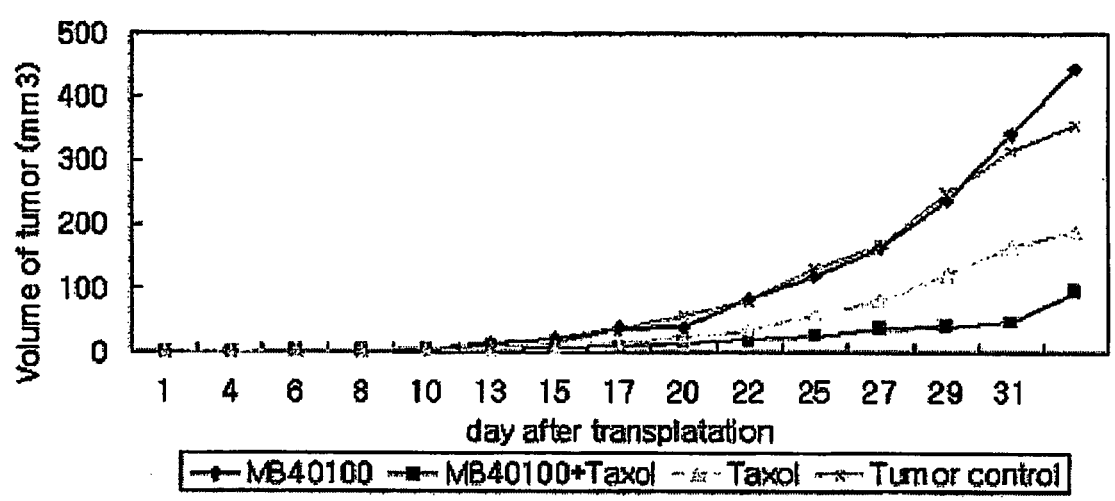
FIG. 17 is a graph showing the increase of anticancer effect by co-administration of an anticancer drug and MB40100 in accordance with EXPERIMENTAL EXAMPLE 11.

The tumor size was measured from 14 to 31 days after injection of tumor. The tumor size in a group where Taxol and MB40100 were co-administered was less than the tumor size in a group where Taxol was administered alone. This shows that the co-administration of MB40100 and anticancer drug has a synergistic effect on the inhibition of solid cancer (refer to FIG. 17).

Experimental Example 12

Preparation of Tablet

| | |
|---|---|
| Corn starch | 34 g |
| Crystalline cellulose | 10 g |
| Brewer's yeast | 40 g |
| Magnesium stearate | 1 g |
| Polysaccharide fraction of PREPARATION EXAMPLE 1 | 15 g |
| Total | 100 g |

Ingredients of the above recipe were evenly mixed and then compressed by a tableting machine so that tablets could be made at 500 mg/tablet.

Experimental Example 13

Preparation of Powder Drug

| | |
|---|---|
| Brewer's yeast | 45 g |
| Magnesium stearate | 5 g |
| Polysaccharide fraction of PREPARATION EXAMPLE 1 | 50 g |
| Total | 100 g |

Ingredients of the above recipe were evenly mixed and then filled in a capsule by an assembly machine so that capsules could be made at 500 mg/capsule.

EFFECT OF THE INVENTION

An extract or polysaccharides according to the present invention, extracted from the leaves and/or stems of plants belonging to *Panax* genus, has an effect on the inhibition of cancer metastasis, whereby it can be used as an drug for cancer treatment, an drug for prophylaxis and treatment of cancer metastasis, and an adjuvant for anticancer drugs and radiation treatment.

Therefore, a composition containing the above extract or polysaccharide fraction has an effect on the overall activation of the immune system, including NKT cells, NK cells, macrophages, T cells, B cells, etc., and the enhancement of the secretion of cytokines associated with anticancer, thereby significantly inhibiting the proliferation and metastasis of cancer cells, so that it can be used as an anticancer and anti-metastasis drug and an adjuvant for general anticancer drugs and radiation treatment by reducing their side effects, such as the decrease of leucocyte numbers.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. An anticancer composition comprising
as an active ingredient an extract isolated by
heating the leaves and/or stems of plants belonging to *Panax quinquefolium* and/or *Panax ginseng* to obtain a crude extract solution;
filtering the crude extract solution;
optionally, concentrating the filtrate; and
precipitating the filtrate with alcohol or acetone, wherein the precipitate is the extract, and
wherein the extract comprises polysaccharides which contain KDO (2-keto-3-deoxyocturosonic acid) and have a molecular weight of 6,000-340,000 Da.

2. The composition according to claim 1, wherein the polysaccharides comprise neutral sugar, and uronic acid.

3. The composition according to claim 2, wherein the sugar composition of the polysaccharides includes rhamnose, fucose, arabinose, xylose, mannose, glucose, galactose, galacturonic acid, glucuronic acid, KDO, and DHA.

4. The composition according to claim 1, wherein the composition has an effect on the inhibition of the proliferation and metastasis of cancer cells.

5. The composition according to claim 1, wherein the composition has a therapeutic and/or prophylactic effect on solid cancers of epithelial or non-epithelial origin.

6. The composition according to claim 1, wherein the composition has a therapeutic and/or prophylactic effect on cancer.

7. The composition according to claim 1, wherein the composition is effective for at least one of the hematopoiesis enhancement, bone marrow defense, immune enhancement, radiation treatment aid, anti-virus, and anti-germ activities.

8. The composition according to claim 7, wherein the composition has the activity of hematopoiesis enhancement.

9. The composition according to claim 7, wherein the composition has the activity of reducing the side effects of general anticancer drugs, including the decrease of leucocytes and thrombocytes.

10. The composition according to claim 7, wherein the composition has the activity of protecting bone marrow and spleen from radiation.

11. The composition according to claim 7, wherein the composition has the activity for enhancement of the activation of immune system cells including NKT cells, NK cells, macrophages, T cells and B cells.

12. The composition according to claim 7, wherein the composition activates NKT cells, NK cells, macrophages, T cells and B cells to secrete tumor necrosis factors, gamma interferon and interleukin 1, being anticancer materials, thereby slowing anticancer, anti-microbial and/or anti-virus activity.

13. The composition according to claim 1, wherein the composition further comprises an anticancer drug(s) and/or an adjuvant(s) therefore.

14. The composition according to claim 13, wherein the anticancer drug is Taxol, Cisplatin, cyclophosphamide, or two or more of the foregoing.

15. The composition according to claim 1, wherein the composition further comprises a carrier or excipient.

16. The composition according to claim 15, wherein the carrier or excipient is the pharmaceutically acceptable one in the form of drink or food.

17. A method of treating cancer comprising administering the composition according to claim 1 in conjunction with an anticancer drug or with radiation therapy to a patient.

18. The method according to claim 17, wherein the anticancer drug is Taxol, Cisplatin, cyclophosphamide, or two or more of the foregoing.

19. The composition according to claim 1 further comprising a pharmaceutically acceptable carrier or excipient.

20. The composition according to claim 19, wherein the composition further comprises an antacid.

21. The composition according to claim 20, wherein the composition is in the form of one of tablet, powder, hard or soft capsule, suspension, solution for injection, emulsion, and non-oral administration form for single or multiple dosage.

22. The composition according to claim 19, wherein the dosage of the active ingredient is in the range of 0.1-6,000 mg/day based upon the average body weight of an adult.

23. The composition according to claim 2, wherein the polysaccharides have a neutral sugar content of 30-80% and a uronic acid content of 10-60%.

24. A method for treating a cancer comprising administering the composition according to claim 1 to a patient.

* * * * *